(12) United States Patent
Lackmann et al.

(10) Patent No.: US 8,637,016 B2
(45) Date of Patent: Jan. 28, 2014

(54) EPHA3 ANTIBODIES FOR THE TREATMENT OF SOLID TUMORS

(75) Inventors: Martin Lackmann, St. Andrews Beach (AU); Andrew Mark Scott, Kew East (AU); Christopher R. Bebbington, San Mateo, CA (US); Geoffrey T. Yarranton, Burlingame, CA (US); Carmelina Murone, Wattle Glen (AU); Catherine To, Bayswater North (AU)

(73) Assignees: KaloBios Pharmaceuticals, Inc., South San Francisco, CA (US); Monash University, Clayton (AU); Ludwig Institute for Cancer Research Limited, New York, NY (US)

( * ) Notice: Subject to any disclaimer, the term of this patent is extended or adjusted under 35 U.S.C. 154(b) by 1273 days.

(21) Appl. No.: 12/045,589

(22) Filed: Mar. 10, 2008

(65) Prior Publication Data

US 2008/0286272 A1    Nov. 20, 2008

Related U.S. Application Data

(60) Provisional application No. 60/893,848, filed on Mar. 8, 2007.

(51) Int. Cl.
*A61K 39/395* (2006.01)

(52) U.S. Cl.
USPC .................. 424/133.1; 424/141.1; 424/142.1; 424/143.1; 424/152.1; 424/172.1

(58) Field of Classification Search
None
See application file for complete search history.

(56) References Cited

U.S. PATENT DOCUMENTS

| | | | | |
|---|---|---|---|---|
| 4,997,913 | A * | 3/1991 | Hellstrom et al. | 424/181.1 |
| 5,811,097 | A * | 9/1998 | Allison et al. | 424/144.1 |
| 6,342,220 | B1 * | 1/2002 | Adams et al. | 424/153.1 |
| 6,652,853 | B2 * | 11/2003 | Welt et al. | 424/133.1 |
| 2002/0090353 | A1 * | 7/2002 | Roussel | 424/85.5 |
| 2003/0091574 | A1 * | 5/2003 | Gevas et al. | 424/155.1 |
| 2004/0180823 | A1 | 9/2004 | Pasquale et al. | |
| 2005/0008649 | A1 | 1/2005 | Shin et al. | |
| 2005/0049194 | A1 | 3/2005 | Frisen et al. | |
| 2005/0255552 | A1 | 11/2005 | Flynn et al. | |
| 2006/0035328 | A1 | 2/2006 | Wang et al. | |
| 2006/0039904 | A1 | 2/2006 | Wu et al. | |
| 2006/0121042 | A1 * | 6/2006 | Dall'Acqua et al. | 424/155.1 |
| 2006/0134098 | A1 | 6/2006 | Bebbington et al. | |

FOREIGN PATENT DOCUMENTS

| | | | |
|---|---|---|---|
| EP | 1508337 | A2 | 2/2005 |
| WO | WO 93/00425 | A1 | 1/1993 |
| WO | WO 03/102144 | A2 | 12/2003 |
| WO | WO 2004/069264 | A1 | 8/2004 |
| WO | WO 2006/052409 | A2 | 5/2006 |

OTHER PUBLICATIONS

Clark (Protein Engineering of Antibody Molecules for Prophylactic and Therapeutic Applications in Man, 1993, pp. 4-5).*
Boyd et al, Journal of Biological Chemistry, 1992, vol. 267, pp. 3262-3267.*
Adams, Ralf H.; "Molecular control of arterial-venous blood vessel identity"; 2003, *J. Anat.*, vol. 202, pp. 105-112.
Bae, Hyun Jin et al.; "Mutational Analysis of the EphA3 Gene in Human Hepatocellular Carcinoma"; 2007, *Korean Society of Toxicogenomics and Toxicoproteomics*, pp. 63.
Booth, Catherine et al.; "Crowd control in the crypt"; 2002, *Nature Medicine*, vol. 8, No. 12, pp. 1360-1361.
Brantley, Dana M. et al.; "Soluble Eph A receptors inhibit tumor angiogenesis and progression in vivo"; 2002, *Oncogene*, vol. 21, pp. 7011-7026.
Brantley, Dana M. et al.; "Eph receptor tyrosine kinases in angiogenesis: From development to disease"; 2004, *Angiogenesis*, vol. 7, pp. 17-28.
Brantley, Dana M. et al.; "Eph receptor tyrosine kinases in Tumor and Tumor Microenvironment"; 2004, *Current Pharmaceutical Design*, vol. 10, pp. 3431-3442.
Cheng, Nikki et al.; "Blockade of EphA Receptor Tyrosine Kinase Activation Inhibits Vascular Endothelial Cell Growth Factor-Induced Angiogenesis"; 2002, *Molecular Cancer Research*, vol. 1, pp. 2-11.
Cheng, Nikki et al.; "Inhibition of VEGF-Dependent Multistage Carcinogenesis by Soluble EphA Receptors"; 2003, *Neoplasma*, vol. 5, No. 5, pp. 445-456.
Davis, Samuel et al.; "Ligands for EPH-Related Receptor Tyrosine Kinases That Require Membrane Attachment or Clustering for Activity"; 1994, *Science*, vol. 266, pp. 816-819.
Dobrzanski, Pawel et al.; "Antiangiogenic and Antitumor Efficacy of EphA2 Receptor Antagonist"; 2004, *Cancer Research*, vol. 64, pp. 910-919.
Hafner, Christian et al.; "Differential Gene Expression of Eph Receptors and Ephrins in Benign Human Tissues and Cancers"; 2004, *Clinical Chemistry*, vol. 50, No. 3, pp. 490-499.
Lackmann, Martin et al.; "Expression and function in modulating tumor cell-cell contacts identifies EphA3 as candidate cell-surface receptor for tumor targeting strategies"; 2004, *Cellular, Molecular, and Tumor Biology*, vol. 45, pp. 1015.
Marme, D.; "VEGFs, Angiopoietins, Ephrins and their Receptors: Putative Targets for Tumor Therapy?"; 2002, *Ann. Hematol.*, vol. 81, pp. S266.
Nakamoto, Masaru et al.; "Diverse Roles for the Eph Family of Receptor Tyrosine Kinases in Carcinogenesis"; 2002, *Microscopy Research and Technique*, vol. 59, pp. 58-67.
Ogawa, Kazushige et al.; "The ephrin-A1 ligand and its receptor, EphA2, are expressed during tumor neovascularization"; 2000, *Oncogene*, vol. 19, pp. 6043-6052.

(Continued)

*Primary Examiner* — Karen Canella
(74) *Attorney, Agent, or Firm* — Kilpatrick Townsend & Stockton LLP

(57) ABSTRACT

The invention provides methods and compositions comprising anti-EphA3 antibodies for the treatment of solid tumors.

30 Claims, 6 Drawing Sheets

(56) References Cited

OTHER PUBLICATIONS

Smith, Fiona M. et al.; "Dissecting the EphA3/Ephrin-A5 Interactions Using a Novel Functional Mutagenesis Screen"; 2004, *The Journal of Biological Chemistry*, vol. 279, No. 10, pp. 9522-9531.

Stein, Elke et al.; "Eph receptors discriminate specific ligand oligomers to determine alternative signaling complexes, attachment, and assembly responses"; 1998, *Genes & Development*, vol. 12, pp. 667-678.

Vaidya, Ashish et al.; "*EphA3* Null Mutants Do Not Demonstrate Motor Axon Guidance Defects"; 2003, *Molecular and Cellular Biology*, vol. 23, No. 22, pp. 8092-8098.

Vearing, Christopher et al.; "Concurrent Binding of Anti-EphA3 Antibody and Ephrin-A5 Amplifies EphA3 Signaling and Downstream Responses: Potential as EphA3-Specific Tumor-Targeting Reagents"; 2005, *Cancer Res.*, vol. 65, No. 15, pp. 6745-6754.

Wimmer-Kleikamp, Sabine H. et al.; "Recruitment Eph receptors into signaling clusters does not require ephrin contact"; 2004, *The Journal of Cell Biology*, vol. 164, No. 5, pp. 661-666.

* cited by examiner

2a

2b

4a

4b

4c

A.

B.

A.

B.

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody IIIA4 heavy chain CDR1 (CDRH1)

<400> SEQUENCE: 1

Ser Tyr Trp Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody IIIA4 heavy chain CDR2 (CDRH2)

<400> SEQUENCE: 2

Asp Ile Tyr Pro Gly Ser Gly Asn Thr Asn Tyr Asp Glu Lys Phe Lys
1               5                  10                  15

Arg

<210> SEQ ID NO 3
<211> LENGTH: 9
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody IIIA4 heavy chain CDR3 (CDRH3)

<400> SEQUENCE: 3

Ser Gly Tyr Tyr Glu Asp Phe Asp Ser
1               5

<210> SEQ ID NO 4
<211> LENGTH: 5
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody FA3AM-H12A and K3D heavy chain CDR1 (CDRH1)

<400> SEQUENCE: 4

Thr Tyr Trp Ile Ser
1               5

<210> SEQ ID NO 5
<211> LENGTH: 17
<212> TYPE: PRT
<213> ORGANISM: Artificial Sequence
```

-continued

```
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody FA3AM-H12A heavy chain CDR2 (CDRH2)

<400> SEQUENCE: 5

Asp Ile Tyr Pro Gly Ser Gly Asn Thr Asn Tyr Asp Glu Lys Phe Gln
1               5                   10                  15

Gly

<210> SEQ ID NO 6
<211> LENGTH: 9
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody FA3AM-H12A and K3D heavy chain CDR3 (CDRH3)

<400> SEQUENCE: 6

Ser Gly Tyr Tyr Glu Glu Phe Asp Ser
1               5

<210> SEQ ID NO 7
<211> LENGTH: 17
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody K3D heavy chain CDR2 (CDRH2)

<400> SEQUENCE: 7

Asp Ile Tyr Pro Gly Ser Gly Asn Thr Asn Tyr Asp Glu Lys Phe Glu
1               5                   10                  15

Gly

<210> SEQ ID NO 8
<211> LENGTH: 11
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody IIIA4 light chain CDR1 (CDRL1)

<400> SEQUENCE: 8

Arg Ala Ser Gln Glu Ile Ser Gly Tyr Leu Gly
1               5                   10

<210> SEQ ID NO 9
<211> LENGTH: 7
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody IIIA4 light chain CDR2 (CDRL2)

<400> SEQUENCE: 9

Ala Ala Ser Thr Leu Asp Ser
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody IIIA4 and FA3AM-H12A light chain CDR3 (CDRL3)

<400> SEQUENCE: 10

Val Gln Tyr Ala Asn Tyr Pro Tyr Thr
1               5

<210> SEQ ID NO 11
<211> LENGTH: 11
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody FA3AM-H12A and K3D light chain CDR1 (CDRL1)

<400> SEQUENCE: 11

Arg Ala Ser Gln Gly Ile Ile Ser Tyr Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody FA3AM-H12A and K3D light chain CDR2 (CDRL2)

<400> SEQUENCE: 12

Ala Ala Ser Ser Leu Gln Ser
1               5

<210> SEQ ID NO 13
<211> LENGTH: 9
<212> TYPE: PRT
<213> ORGANISM: Artificial Sequence
<220> FEATURE:
<223> OTHER INFORMATION: mouse anti-ephrin receptor EphA3 (ephrin type-A
      receptor 3, human embryo kinase 1 (HEK, HEK4), eph-like tyrosine
      kinase 1 (ETK1), tyrosine-protein kinase TYRO4) monoclonal
      antibody K3D light chain CDR3 (CDRL3)

<400> SEQUENCE: 13

Val Gln Tyr Met Asn Tyr Pro Tyr Thr
1               5
```

EPHA3 ANTIBODIES FOR THE TREATMENT OF SOLID TUMORS

CROSS-REFERENCE TO RELATED APPLICATIONS

This application claims benefit of U.S. provisional application No. 60/893,848, filed Mar. 8, 2007, which application is herein incorporated by reference.

BACKGROUND OF THE INVENTION

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov, et al., *Dev Cell* 7:465-80, 2004). In contrast to other receptor tyrosine kinases, Eph receptor activation does not only require ligand binding and dimerization, but also involves preformed ligand oligomers. Thus, tyrosine phosphorylation of Eph receptors requires presentation of ephrin ligands in their clustered or membrane-attached forms (Davis et al., *Science* 266:816-819, 1994). Functional and biochemical Eph responses occur at higher ligand oligomerization states (Stein et al., *Genes Dev* 12:667-678, 1998).

Among other patterning functions, various Ephs and ephrins have been shown to play a role in vascular development. Knockout of EphB4 and ephrin-B2 results in a lack of the ability to remodel capillary beds into blood vessels (Poliakov, et al., supra) and embryonic lethality. Persistent expression of some Eph receptors and ephrins has also been observed in newly-formed, adult micro-vessels (Brantley-Sieders, et al., *Curr Pharm Des* 10:3431-42, 2004; Adams, *J Anat* 202:105-12, 2003).

The de-regulated re-emergence of some ephrins and their receptors in adults also has been observed to contribute to tumor invasion, metastasis and neo-angiogenesis (Nakamoto, et al., *Microsc Res Tech* 59:58-67, 2002; Brantley-Sieders, et al., surpa). Furthermore, some Eph family members have been found to be over-expressed on tumor cells from a variety of human tumors (Brantley-Sieders, D. et al., supra); Marme, *Ann Hematol* 81 Suppl 2:S66, 2002; Booth, et al., *Nat Med* 8:1360-1, 2002).

Dominant-negative, soluble EphA2 or A3 proteins exhibit effects on ephrin-induced endothelial cell functions in vitro, and tumor angiogenesis and progression in vivo (Brantley, et al. *Oncogene* 21:7011-26, 2002; Cheng, et al. *Neoplasia* 5:445-56, 2003; Dobrzanski, et al. *Cancer Res* 64:910-9, 2004). However, because of lack of specificity of ephrin-A family members for Eph A receptors, these studies do not indicate whether EphA3 itself plays a role in the vascular endothelium in either tumor or normal tissues.

In summary, prior to the current invention, there has been no evidence that EphA3 is expressed on endothelial cells present in the tumor vasculature. Indeed, no vasculature abnormalities have been reported in EphA3 knockout mice (see, e.g., Vaidya et al. *Mol. Cell. Biol.* 23:8092-8098, 2003). Thus, although certain Eph receptors and ephrins have been implicated as playing a role in angiogenesis and tumor formation and progression, there have been no specific therapies that target EphA3 expression on tumor endothelial cells. This invention therefore provides new therapeutic targets and methods of treating tumors.

BRIEF SUMMARY OF THE INVENTION

The invention is based on the discovery that EphA3 is expressed on the vasculature of solid tumors. Thus, in one aspect, the invention provides a method of inhibiting growth of a solid tumor that does not express EphA3 on tumor cells, the method comprising administering an anti EphA3 antibody. In some embodiments, the anti EphA3 antibody clusters EphA3, e.g., through Fc receptor binding, on the surface of cells that express it, particularly endothelial cells of the vasculature of a tumor. In some embodiments, the EphA3 antibody activates EphA3, even when a natural ligand is bound to EphA3.

The invention also provides a method of inhibiting tumor growth, comprising administering to a patient that has a solid tumor: a) an anti-EphA3 antibody that clusters EphA3, e.g., through Fc receptor binding, and b) a cancer therapeutic agent. In some embodiments, the cancer therapeutic agent disrupts tubulin assembly. The therapeutic agent can be administered concurrently with the anti EphA3 antibody, or following treatment with the anti-EphA3 antibody. In some embodiments, the therapeutic agent is covalently linked to the anti-EphA3 antibody. In other embodiments, the therapeutic agent is a separate molecule that is not linked to the EphA3 antibody. In some embodiments, the anti EphA3 antibody competes for EphA3 binding with monoclonal antibody IIIA4 (mAb IIIA4) and clusters EphA3. In some embodiments, the antibody activates EphA3.

In another aspect, the invention provides a composition comprising an anti EphA3 antibody having an active human isotype, where the antibody clusters EphA3, e.g., through Fc receptor binding. In one embodiment, the anti EphA3 antibody competes with mAb IIIA4 for binding to EphA3. In some embodiments, the antibody competes with mAb IIIA4 for binding to EphA3 and does not block binding of an ephrin, e.g., ephrin-A5, to EphA3. In another embodiment, the antibody binds to EphA3 and clusters EphA3, but does not compete with mAb IIIA4 for binding to EphA3. In some embodiments, the antibody activates EphA3. A composition of the invention can also include another agent that inhibits tumor growth, e.g., an agent that inhibits tubulin assembly.

An anti-EphA3 antibody for use in the methods and/or compositions of the invention can be a recombinant or chimeric antibody. In another embodiment, the antibody is a human antibody, e.g., a humaneered antibody or a humanized antibody. In a further embodiment, the antibody is a polyclonal antibody. Alternatively, the antibody can be a monoclonal antibody. In an additional embodiment, the antibody is a multivalent antibody that comprises an antibody fragment that is a Fab, a Fab', or an Fv. In another embodiment, the antibody has an active human isotype, e.g., IgG1, IgG3, IgM, IgA, or IgE, that binds to Fc receptors on immune effector cells. Thus, in some embodiments the antibody comprises a human heavy chain constant region, e.g., an IgG1 or IgG3 gamma region. In some embodiments, the antibody may be chemically cross-linked IgG.

In some embodiments, an antibody for use in the methods and/or compositions of the invention comprises the $V_H$ and $V_L$ regions of mAb IIIA4. In other embodiments, the antibody comprises the $V_H$ and $V_L$ region CDR1, CDR2 and CDR3 of mAb IIIA4. In further embodiments, the antibody comprises the $V_H$ region CDR3 and $V_L$ region CDR3 of mAb IIIA4. In some embodiments, the antibody comprises a heavy chain CDR1, CDR2, and CDR3 from Table 1 and a light chain CDR1, CDR2, and CDR3 from Table 1. In additional embodiments, the antibody comprises a heavy chain CDR3 from Table 1 and a light chain CDR3 from Table 1.

The invention additionally provide a method of inhibiting the growth of solid tumors (whether or not the tumor cells express EpA3) by administering a monomeric, non-aggregated antibody preparation, where the antibody can cluster EphA3. Such antibodies, e.g., have an active isotype, e.g., have a human IgG1 or IgG3 gamma region. In some embodiments, the antibody activates EphA3. The antibody can be a recombinant or chimeric antibody. In another embodiment, the antibody is a human antibody, e.g., a humaneered antibody or a humanized antibody. In some embodiments, the antibody is a Fab, a Fab', or an Fv that is in a multivalent form, e.g., a tri-Fab. In some embodiments, an antibody for use in the methods and/or compositions of the invention comprises the $V_H$ and $V_L$ regions of mAb IIIA4. In other embodiments, the antibody comprises the $V_H$ and $V_L$ region CDR1, CDR2 and CDR3 of mAb IIIA4; or a heavy chain CDR1, CDR2 and CDR3 from Table 1 and a light chain CDR1, CDR2, and CDR3 from Table 1. In further embodiments, the antibody comprises the $V_H$ region CDR3 and $V_L$ region CDR3 of mAb IIIA4. In additional embodiments, the antibody comprises a heavy chain CDR3 from Table 1 and a light chain CDR3 from Table 1.

In some embodiments, the invention provides a method of inhibiting the growth of solid tumors by administering an antibody to EphA3 that clusters EphA3, e.g., through Fc receptor binding, present on tumor vascular endothelial cells with the proviso that antibody is not conjugated to a therapeutic agent such as a radiometal or toxin. In some embodiments, the antibody activates EphA3.

In some embodiments, the invention provides a method of inhibiting the growth of solid tumors by administering an antibody to EphA3 that is chemically cross-linked.

In another aspect, the invention provides a method of treating solid tumors that comprises administering a smaller dose of antibody compared to treatment regimens that target proteins on the surface of tumor cells. The method targets the EphA3 receptors present on tumor vasculature endothelial cells. Accordingly, an antibody can be administered at a dose of less than about 1.0 mg/kg, preferably less than about 0.5 mg/kg, or less than 0.1 mg/kg, to inhibit growth of the tumor. Such an antibody can be any antibody of the invention as described herein that binds to and clusters EphA3. In some embodiments, the antibody activates EphA3.

The invention also provides a method of inhibiting tumor growth by administering an EphA3 binding agent, e.g., a multivalent form of a scaffolded protein, or an antibody, that specifically binds to EphA3 and clusters, the EphA3 receptor. In typical embodiments, clustering induced by an EphA3 binding agent such as an antibody can take place even when natural ligand, for example and ephrin such as ephrin-A5, is bound to EphA3. The binding agent can be a multivalent form of scaffolded proteins that bind to EphA3. In some embodiments, the EphA3 binding agent competes with mAb IIIA4 for binding to EphA3. Administration of anti-EphA3 binding agents to tumors is exemplified by the use of anti-EphA3 antibodies. However, the methods described herein can also be used for other anti-EphA3 binding agents.

The EphA3 binding agents of the invention, e.g., an EphA3 antibody that clusters EphA3 receptors, can also be used for the treatment of other diseases that involve neovascularization. For example, an EphA3 antibody related as described herein can be used for the treatment of retinal vascular diseases, such as age-related macular degeneration or other intraocular neovascular syndromes. Thus, other non-neoplastic conditions that can be treated with the EphA3 agents described herein include rheumatoid arthritis, psoriasis, atherosclerosis, diabetic and other proliferative retinopathies including retinopathy of prematurity, retrolental fibroplasia, neovascular glaucoma, age-related macular degeneration, thyroid hyperplasias (including Grave's disease), hemangiomas, corneal and other tissue transplantation, preeclampsia, and chronic inflammation.

DETAILED DESCRIPTION OF THE INVENTION

Definitions

Figures 1A, 1B, 1C:
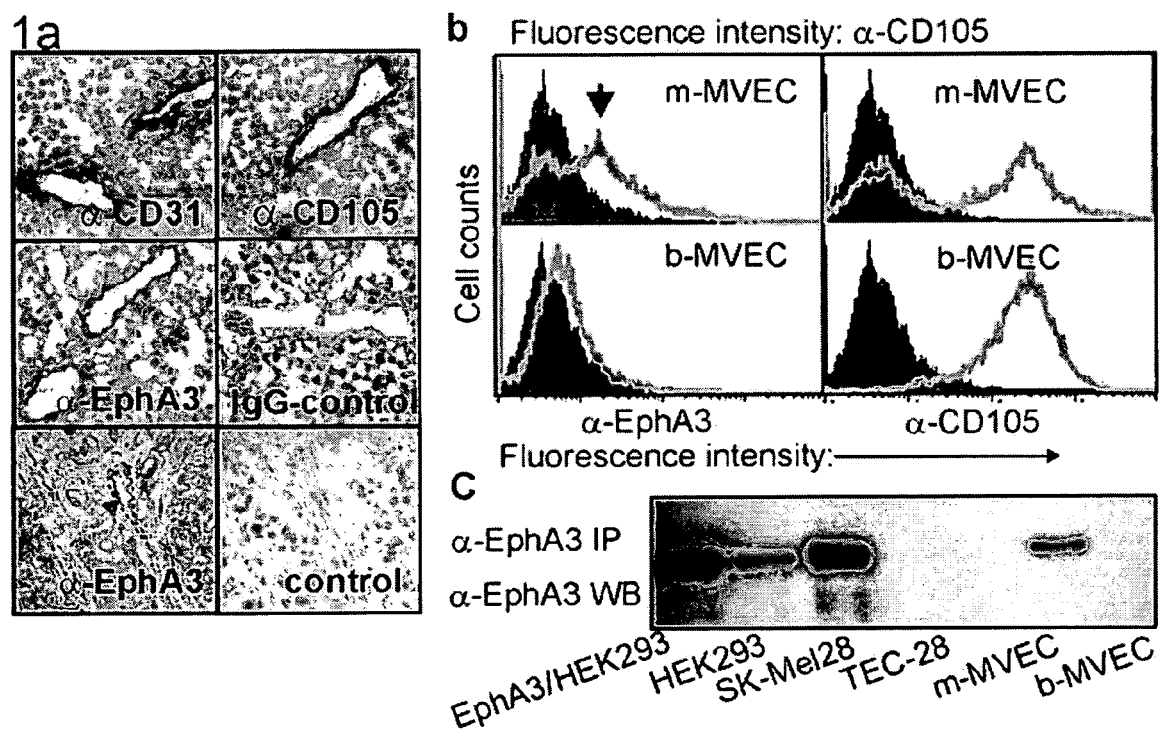
FIGS. 1a-c. Detection of EphA3 using the EphA3 monoclonal antibody IIIA4 (mAb IIIA4) in (a) human malignant melanoma sections or (b), by analysis of various endothelial cell lines using flow cytometry, and (c) by IP/Western Blot analysis of parental or EphA3-overexpressing HEK293T cells, SK-Mel melanoma cells, TEC-28 kidney tumor endothelial cells, brain microvascular endothelial cells (b-MVEC) or myometrial MVECS (m-MVEC).

As used herein "solid tumor" refers to an abnormal mass of tissue. Solid tumors may be benign or malignant. Solid tumors that can be treated using the methods and compositions of the invention are characterized by neovascularization. The tumor vasculature (also referred to as microvasculature) is characterized by rapid proliferation of the endothelial cells, poor wall structure, increased permeability to plasma proteins, and a limited ability to increase blood flow in response to demand. The tumor vasculature allows the tumor cells of the tumor mass to acquire a growth advantage compared to the normal cells. Solid tumors are named for the type of cells that form them. Examples of solid tumors are sarcomas, carcinomas (epithelial tumors), melanomas, and glioblastomas.

"Inhibiting growth of a tumor" in the context of the invention refers to slowing tumor growth and/or reducing tumor size. "Inhibiting growth of a tumor" thus includes killing tumor cells as well as slowing or arresting tumor cell growth.

The term "tumor cell" as used herein refers to a neoplastic cell. The term includes cancer cells that are benign as well as malignant. Neoplastic transformation is associated with phenotypic changes of the tumor cell relative to the cell type from which it is derived. The changes can include loss of contact inhibition, morphological changes, and aberrant growth. (see, Freshney, *Culture of Animal Cells a Manual of Basic Technique* ($3^{rd}$ edition, 1994). In the context of the current invention, a "tumor cell" does not refer to the cells of the vasculature of the tumor.

As used herein, "tumor vasculature endothelial cells" are endothelial cells that are present in the vasculature of a tumor.

As used herein "EphA3" refers to the Eph receptor A3. This receptor has also been referred to as "Human embryo kinase", "hek", "eph-like tyrosine kinase 1", "etk1" or "tyro4". EphA3 belongs to the ephrin receptor subfamily of the protein-tyrosine kinase family. EPH and EPH-related receptors have been implicated in mediating developmental events. Receptors in the EPH subfamily typically have a single kinase domain and an extracellular region containing a Cys-rich domain and 2 fibronectin type III repeats. The ephrin receptors are divided into 2 groups based on the similarity of their extracellular domain sequences and their affinities for binding ephrin-A and ephrin-B ligands. EphA3 binds ephrin-A ligands. EphA3 nucleic acid and protein sequences are known. An exemplary human EphA3 amino acid sequence is available under accession number (EAW68857).

In the present invention, "activation" of EphA3 causes phosphorylation of EphA3 and typically, rounding of the cell.

As used herein, "clustering" or "cross-linking" of EphA3 refers to cross-linking of EphA3 molecules on the surface of a cell. Clustering generally forms an active signaling complex that causes phosphorylation of EphA3. "Clustering" is typically a hallmark of EphA3 activation.

The term "non-aggregated" as used herein with reference to a preparation of an antibody that has an active isotype refers to a preparation that has less than about 5%, and in some embodiments less than about 2%, or less than about 1%, of the antibody in an aggregated form, i.e., that is in a form that is more than monomeric.

A "monomeric" antibody as used herein refers to a divalent antibody that has two antigen binding sites.

A "multivalent" antibody or "multivalent" binding agent as used herein refers to an antibody or protein that has more than two antigen binding sites.

A "solid tumor that does not express EphA3 on tumor cells" as used herein refers to a solid tumor that has fewer than about 25% of cells that express EphA3 on the tumor cell. In some embodiments, the solid tumor has fewer than about 15%, or fewer than 10%, or fewer than 5% of cells that express EphA3 on the tumor cell. In further embodiments, a tumor cell that does not express EphA3 refers to a tumor cell that has little or no detectable EphA3 expression, e.g., as detected by immunohistochemistry. "Little detectable EphA3 expression" refers an amount of expression that is less than 2 times the background from a control cell that does not express EphA3.

In the present invention, "EphA3 antibody" or "anti EphA3 antibody" are used interchangeably to refer to an antibody that binds to EphA3. In some embodiments, the antibody clusters EphA3, e.g., through Fc receptor binding. The term encompasses antibodies that bind to EpbA3 in the presence of ephrin ligand (e.g., ephrin-A5) binding, as well as antibodies that bind to the ligand binding site.

An "EphA3 antibody that binds to EphA3 in the presence of binding of an ephrin ligand" refers to an antibody that does not significantly prevent binding of an ephrin ligand, such as ephrin-A5, to EphA3. The presence of such an antibody in a binding reaction comprising EphA3 and an ephrin ligand, e.g., ephrin-A5, reduces ephrin ligand binding to EphA3 by less than about 30%, typically less than 20% or 10%.

The term "mAb IIIA4" refers to monoclonal antibody IIIA4 that was originally raised against LK63 human acute pre-B leukemia cells to affinity isolate EphA3 (Boyd, et al. *J Biol Chem* 267:3262-3267, 1992). mAb IIIA4 binds to the native EphA3 globular ephrin-binding domain (e.g., Smith, et al., *J. Biol. Chem* 279:9522-9531, 2004). It is deposited in the European Collection of Animal Cell Cultures under accession no. 91061920 (see, e.g., EP patent no. EP0590030).

An "antibody having an active isotype" as used herein refers to an antibody that has a human Fc region that binds to an Fc receptor present on immune effector cells. "Active isotypes" include IgG1, IgG3, IgM, IgA, and IgE. The term encompasses antibodies that have a human Fc region that comprises modifications, such as mutations or changes to the sugar composition and/or level of glycosylation, that modulate Fc effector function.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., *Science* 247:306-1310, 1990).

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein includes antibody fragments that retain binding specificity. For example, there are a number of well characterized antibody fragments. Thus, for example, pepsin digests an antibody below the disulfide linkages in the hinge region to produce F(ab)'$_2$, a dimer of Fab which itself is a light chain joined to VH—CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, e.g., using recombinant techniques, as soluble proteins or as fragments obtained from display methods. Antibodies can also include diantibodies and miniantibodies. Antibodies of the invention also include heavy chain dimers, such as antibodies from camelids. For the purposes of this invention, antibodies are employed in a form that can cluster EphA3 present on the surface of endothelial cells. Thus, in some embodiments an antibody is in a monomeric form that has an active isotype. In other embodiments the antibody is in a multivalent form, e.g., a trivalent or tetravalent form, that can cross-link EphA3.

As used herein, "V-region" refers to an antibody variable region domain comprising the segments of Framework 1, CDR1, Framework 2, CDR2, and Framework3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human $V_H$ segments J. Mol. Biol. 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.*, 262 (5), 732-745 (1996); and Martin et al, *Proc. Natl. Acad. Sci. USA*, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in which the CDRs of a recipient human antibody are replaced by CDRs from a donor non-human antibody. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., Nature 321:522-525; 1986; Riechmann et al., Nature 332:323-327, 1988; Verhoeyen et al., Science 239:1534-1536, 1988); Presta, Curr. Op. Struct. Biol. 2:593-596, 1992; U.S. Pat. No. 4,816,567), including techniques such as "superhumanizing" antibodies (Tan et al., J. Immunol. 169: 1119, 2002) and "resurfacing" (e.g., Staelens et al., Mol. Immunol. 43: 1243, 2006; and Roguska et al., Proc. Natl. Acad. Sci. USA 91: 969, 1994).

A "humaneered" antibody in the context of this invention refers to is an engineered human antibody having a binding specificity of a reference antibody. The term refers to an immunoglobulin molecule that contains minimal sequence derived from the reference antibody. Typically, an antibody is "humaneered" by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. Methods for humaneering are provided in US patent application publication no. 20050255552 and US patent application publication no. 20060134098.

A "human" antibody as used herein encompasses humanized and humaneered antibodies, as well as human monoclonal antibodies that are obtained using known techniques.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein refers to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus, an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins, such as a cell extract. Thus, under designated immunoassay conditions, the specified antibodies bind to a particular protein sequence at least two times the background and more typically more than 10 to 100 times background.

As used herein, "cancer therapeutic agent" refers to an agent that when administered to a patient suffering from cancer, in a therapeutically effective dose, will cure, or at least partially arrest the symptoms of the disease and complications associated with the disease.

The terms "identical" or percent "identity," in the context of two or more polypeptide (or nucleic acid) sequences, refer to two or more sequences or subsequences, e.g., an antibody sequence, that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids=in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., Nuc. Acids Res. 25:3389-3402

(1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

An indication that two polypeptides are substantially identical is that the first polypeptide is immunologically cross reactive with the antibodies raised against the second polypeptide. Thus, a polypeptide is typically substantially identical to a second polypeptide, e.g., where the two peptides differ only by conservative substitutions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Introduction

The present invention relates to methods of inhibiting tumor growth by administering an anti-EphA3 antibody to a patient that has a solid tumor. The invention is based, in part, on the discovery that EphA3 is expressed on the endothelial cells of the vasculature of solid tumors and can be used as a target to inhibit growth of the tumor, even in the absence of tumor cells that express EphA3. Thus, in the current invention, the anti-EphA3 antibodies that are administered bind to the tumor vasculature.

The methods of the invention comprises administering an anti-EphA3 antibody that clusters EphA3. In some embodiments, such an antibody activates EphA3 tyrosine kinase activity. Not to be bound by theory, this results in signal transduction that leads to re-arrangement of the cytoskeleton and cell-rounding as described in US patent application 20060140957.

In some embodiments, an anti-EphA3 antibody for use in this invention does not block binding of EphA3 to ephrin, e.g., ephrin-A5, and is able to cluster the ephrin receptor. In some embodiments, the antibody competes with Mab IIIA4 for binding to EphA3. Such antibodies often bind to the same epitope as Mab IIIA4. In additional embodiments, the antibody has an active isotype where the heavy chain constant domain can bind to Fc receptor present on immune effector cells.

An anti-EphA3 antibody as described herein can also be used to treat tumors that express EphA3 on the surface of the tumor cell in addition to expressing EphA3 on the vasculature.

Anti-EphA3 Antibodies

Various anti-EphA3 antibodies can be used in the methods of the invention. Such antibodies bind to EphA3 and cluster the receptor. In some embodiments, the antibody activates EphA3. The anti-EphA3 antibodies of the invention can be raised against EphA3 proteins, or fragments, or produced recombinantly. Any number of techniques can be used to determine antibody binding specificity. See, e.g., Harlow & Lane, Antibodies, A Laboratory Manual (1988) for a description of immunoassay formats and conditions that can be used to determine specific immunoreactivity of an antibody In some embodiments, the anti-EphA3 antibody is a polyclonal antibody. Methods of preparing polyclonal antibodies are known to the skilled artisan (e.g., Harlow & Lane, Antibodies, A Laboratory manual (1988); Methods in Immunology). Polyclonal antibodies can be raised in a mammal by one or more injections of an immunizing agent and, if desired, an adjuvant. The immunizing agent includes a EphA3 receptor protein, or fragment thereof.

In some embodiments, the anti-EphA3 antibody is a monoclonal antibody. Monoclonal antibodies may be prepared using hybridoma methods, such as those described by Kohler & Milstein, Nature 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

Human monoclonal antibodies can be produced using various techniques known in the art, including phage display libraries (Hoogenboom & Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

In some embodiments the anti-EphA3 antibodies are chimeric or humanized monoclonal antibodies. As noted supra, humanized forms of antibodies are chimeric immunoglobulins in which a CDR of a human antibody is replaced by a CDR of a non-human species such as mouse, rat or rabbit having the desired specificity, affinity and capacity.

An antibody that is employed in the invention can be in numerous formats. In some embodiments, the antibody can include an Fc region, e.g., a human Fc region. For example, such antibodies include IgG antibodies that bind EphA3 and that have an active isotype. In some embodiments, the antibody can be an active (i.e., it can cluster EphA3) fragment or derivative of an antibody such as an Fab, Fab', F(ab')$_2$, Fv, scFv, or a single domain antibody ("dAb"). Other exemplary embodiments of antibodies that can be employed in the invention include activating nanobodies or activating camellid antibodies. Such antibodies may additionally be recombinantly engineered by methods well known to persons of skill in the art. As noted above, such antibodies can be produced using known techniques. As appreciate by one of skill in the art, in some embodiments, when an antibody is in a format that can be monovalent, e.g., an Fv or Fab format, the antibody is employed as a multivalent antibody, such as a trivalent or tetravalent antibody. For example, a trivalent Fab could be used. Methods of generating multivalent antibodies are known (see, e.g., King et al., Cancer Res. 54:6176-6185, 1994). Further, if a divalent fragment such as a F(ab')$_2$ fragment is employed, such a fragment is in a format that can cluster EphA3 receptors on the surface of a cell, e.g., an antibody format in which a region that can interact with an effector molecule is retained such as where the divalent antibody is linked to an active Fc region that can bind to Fc receptors present on immune effector cells such as T-cells, macrophages, neutrophils, mast cells, and the like.

In many embodiments, an antibody for use in the invention has an Fc constant region that has an effector function, e.g., binds to an Fc receptor present on immune effector cells. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor), and the like. Such effector functions generally require the Fc region to be combined with a binding domain (e.g. an antibody variable domain) and can be assessed using known assays (see, e.g., the references cited hereinbelow.)

Not to be bound by theory, anti-EphA3 antibodies with an active isotype, e.g., that are capable of binding Fc-receptors, can induce cell-rounding of endothelial cells expressing EphA3 in vivo leading to direct disruption of the tumor vasculature. It is believed that rounding of the endothelial cells leads to disruption of the tubular structure of the blood vessel and collapse of the capillary due to the high hydrostatic pressure within the tumor.

Anti-EphA3 antibodies that have an active isotype and are bound to Fc-receptors on effector cells, such as macrophages, monocytes, neutrophils and NK cells, can also induce disruption of tumor vasculature by antibody mediated cellular cytotoxicity (ADCC).

The Fc region can be from a naturally occurring IgG1, or other active isotypes, including IgG3, IgM, IgA, and IgE. "Active isotypes" include antibodies where the Fc region comprises modifications to increase binding to the Fc receptor or otherwise improve the potency of the antibody. Such an Fc constant region may comprise modifications, such as mutations, changes to the level of glycosylation and the like, that increase binding to the Fc receptor. There are many methods of modifying Fc regions that are known in the art. For example, U.S. Patent Application Publication No. 20060039904 describes variants of Fc receptors that have enhanced effector function, including modified binding affinity to one or more Fc ligands (e.g., FcγR, C1q). Additionally, such Fc variants have altered antibody-dependent cell-mediated cytotoxicity (ADCC) and/or complement dependent cytotoxicity (CDC) activity. Other Fc variants include those disclosed by Ghetie et al., Nat. Biotech. 15:637-40, 1997; Duncan et al, Nature 332:563-564, 1988; Lund et al., J. Immunol 147:2657-2662, 1991; Lund et al, Mol Immunol 29:53-59, 1992; Alegre et al, Transplantation 57:1537-1543, 1994; Hutchins et al., *Proc Natl. Acad Sci USA* 92:11980-11984, 1995; Jefferis et al, *Immunol Lett.* 44:111-117, 1995; Lund et al., *FASEB J* 9:115-119, 1995; Jefferis et al, *Immunol Lett* 54:101-104, 1996; Lund et al, *J Immunol* 157:4963-4969, 1996; Armour et al., *Eur J Immunol* 29:2613-2624, 1999; Idusogie et al, *J Immunol* 164:4178-4184, 200; Reddy et al, *J Immunol* 164:1925-1933, 2000; Xu et al., *Cell Immunol* 200:16-26, 2000; Idusogie et al, *J Immunol* 166:2571-2575, 2001; Shields et al., *J Biol Chem* 276:6591-6604, 2001; Jefferis et al, *Immunol Lett* 82:57-65. 2002; Presta et al., *Biochem Soc Trans* 30:487-490, 2002; Lazar et al., *Proc. Natl. Acad. Sci. USA* 103:4005-4010, 2006; U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091; and PCT Publications WO 94/2935; WO 99/58572; WO 00/42072; WO 02/060919, and WO 04/029207, In some embodiments, the glycosylation of Fc regions may be modified. for example, a modification may be glycosylation, for example, by altering one or more sites of glycosylation within the antibody sequence. Such an approach is described in further detail in U.S. Pat. Nos. 5,714,350 and 6,350,861. An Fc region can also be made that has an altered type of glycosylation, such as a hypofucosylated Fc variant having reduced amounts of fucosyl residues or an Fc variant having increased bisecting GlcNAc structures. Such carbohydrate modifications can be accomplished by, for example, expressing the antibody in a host cell with altered glycosylation machinery. Cells with altered glycosylation machinery, including yeast and plants, have been described in the art and can be used as host cells in which to express recombinant antibodies of the invention to thereby produce an antibody with altered glycosylation. Techniques for modifying glycosylation include those disclosed e.g., in Umana et al, *Nat. Biotechnol* 17:176-180, 1999; Davies, et al., *Biotechnol. Bioeng.* 74:288-294, 2001; Shields et al, *J Biol Chem* 277: 26733-26740, 2002; Shinkawa et al., *J Biol Chem* 278:3466-3473, 2003; Niwa et al. *Clinc. Cancer Res.* 1:6248-6255, 2004; Presta et al., *Biochem Soc Trans* 30:487-490, 2002; Kanda et al, *Glycobiology* 17:104-118, 2006; U.S. Pat. Nos. 6,602,684; 6,946,292; and 7,214,775; U.S. Patent Application Publication Nos. 20070248600; 20070178551; 20080060092; 20060253928; PCT publications WO 00/61739; WO 01/292246; WO 02/311140; and WO 02/30954; and Potillegent™ technology (Biowa, Inc. Princeton, N.J.); and GlycoMAb™. glycosylation engineering technology (GLYCART biotechnology AG, Zurich, Switzerland).

In some embodiments of the invention, the antibody is additionally engineered to reduce immunogenicity, e.g., so that the antibody is suitable for repeat administration. Methods for generating antibodies with reduced immunogenicity include humanization and humaneering procedures and modification techniques such as de-immunization, in which an antibody is further engineered, e.g., in one or more framework regions, to remove T cell epitopes.

In some embodiments, the antibody is a humaneered antibody. A humaneered antibody is an engineered human antibody having a binding specificity of a reference antibody, obtained by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. Methods for humaneering are provided in US patent application publication no. 20050255552 and US patent application publication no. 20060134098.

An antibody can further be de-immunized to remove one or more predicted T-cell epitopes from the V-region of an antibody. Such procedures are described, for example, in WO 00/34317.

In some embodiments, the variable region is comprised of human V-gene sequences. For example, a variable region sequence can have at least 80% identity, or at least 85% or at least 90% identity, to human germ-line V-gene sequences.

An antibody used in the invention can include a human constant region. The constant region of the light chain may be a human kappa or lambda constant region. The heavy chain constant region is often a gamma chain constant region, for example, a gamma-1 or gamma-3 constant region.

In some embodiments, e.g., where the antibody is a fragment, the antibody can be conjugated to another molecule, e.g., to provide an extended half-life in vivo such as a polyethylene glycol (pegylation) or serum albumin. Examples of PEGylation of antibody fragments are provided in Knight et al., *Platelets* 15:409, 2004 (for abciximab); Pedley et al., *Br. J. Cancer* 70:1126, 1994 (for an anti-CEA antibody); and Chapman et al., *Nature Biotech.* 17:780, 1999.

Antibody Specificity

An antibody for use in the invention binds to EphA3, which typically leads to clustering of EphA3. An exemplary antibody suitable for use with the present invention is mAb IIIA4. This antibody binds to the native EphA3 globular ephrin-binding domain (Smith et al., *J. Biol. Chem.* 279:9522-9531, 2004; and Vearing et al., *Cancer Res.* 65:6745-6754, 2005). High affinity mAb IIIA4 binding to the EphA3 surface has little effect on the overall affinity of ephrin-A5 interactions with EphA3.

In some embodiments, a monoclonal antibody that competes with mAb IIIA4 for binding to EphA3, or that binds the same epitope as mAb IIIA4, is used. Any of a number of competitive binding assays can be used to measure competition between two antibodies for binding to the same antigen. For example, a sandwich ELISA assay can be used for this purpose. In an exemplary assay, ELISA is carried out by using a capture antibody to coat the surface of a well. A subsaturating concentration of tagged-antigen is then added to the capture surface. This protein will be bound to the antibody through a specific antibody: antigen interaction. After washing, a second antibody that is linked to a detectable moiety is added to the ELISA. If this antibody binds to the same site on the antigen as the capture antibody, or interferes with binding to that site, it will be unable to bind to the target protein as that site will no longer be available for binding. If however this second antibody recognizes a different site on the antigen it will be able to bind. Binding can be detected by quantifying the amount of detectable label that is bound. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine specificity. The ability of a particular antibody to recognize the same epitope as another antibody is typically determined by such competition assays.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Binding Affinity

In some embodiments, the antibodies suitable for use with the present invention have a high affinity binding for human EphA3. For the purposes of this invention, high affinity binding between an antibody and an antigen exists if the dissociation constant ($K_D$) of the antibody is <about 10 nM, for example, about 5 nM, or about 2 nM, or about 1 nM, or less. A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany) using CM5 sensor chips, as described by Krinner et al., (2007) *Mol. Immunol. February;* 44(5):916-25. (Epub 2006 May 11)).

The anti-EphA3 antibody can bind to any region of EphA3. Often, the antibody clusters EphA3. Antibodies that cluster EphA3 have an active human isotype, such as an IgG1, IgG3, IgM, IgA, or IgE. Antibodies that cluster EphA3 can also be multivalent, i.e., in the context of this invention, have more than two antigen binding sites, including forms of monomers that are cross-linked or otherwise multimerized to form multivalent antibodies. In some embodiments, the anti-EphA3 antibody activates EphA3.

In some embodiments, an antibody employed in the invention does not compete with an EphA3 ligand for binding to EphA3, whereas in other embodiments an EphA3 antibody for use in the invention can compete for binding of an EphA3 ligand such as an ephrin, e.g., ephrin-A5, to EphA3. Antibodies that compete with a ligand for binding to EphA3, can be identified using techniques as described above, where an ephrin ligand such as ephrin-A5, is used instead of another antibody for a competition analysis.

In exemplary embodiments, the anti-EphA3 antibody comprises the $V_L$ and $V_H$ regions of mAb IIIA4. In other embodiments, the anti-EphA3 antibody comprises CDRs 1, 2 and 3 of mAb IIIA4. In some embodiments, the anti-EphA3 antibody comprises CDR3 of mAb IIIA4. Table 1 provides CDR sequences (defined according to Kabat numbering) of antibodies that bind to the same epitope as mAb IIIA4. Affinity for EphA3 antigen was determined by ELISA. An antibody of the invention may thus also have heavy chain and/or lights chain CDRs set forth in Table 1.

Non-Antibody EphA3 Binding Agents

Other proteins that bind to EphA3 and cross-link the EphA3 receptor may also be administered to a patient that has a solid tumor. In some embodiments, the solid tumor does not express EphA3 on the surface of the tumor cells, but expresses EphA3 on the vasculature. Such proteins include a soluble Ephrin A5-Fc protein.

Other EphA3 binding agents include scaffolded proteins that bind EphA3. Thus, the EphA3 binding agent can be an "antibody mimetic" that targets and binds to the antigen in a manner similar to antibodies. When an antibody mimetic is used, the form of the mimetic is such that it clusters EphA3. For example, the antibody mimetic is used in a multivalent format.

Certain antibody mimetics use non-immunoglobulin protein scaffolds as alternative protein frameworks for the variable regions of antibodies. For example, Ku et al. (*Proc. Natl. Acad. Sci. U.S.A.* 92:6552-6556, 1995) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies.

U.S. Pat. Nos. 6,818,418 and 7,115,396 disclose an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96:1898-1903, 1999) disclose an antibody mimic based on a lipocalin scaf-

TABLE 1

| antibody | CDRH1 | CDRH2 | CDRH3 | AFFINITY (nM) |
|---|---|---|---|---|
| IIIA4 | SYWIN (SEQ ID NO: 1) | DIYPGSGNTNYDEKFKR (SEQ ID NO: 2) | SGYYEDFDS (SEQ ID NO: 3) | 2.5 |
| FA3AM-H12A | TYWIS (SEQ ID NO: 4) | DIYPGSGNTNYDEKFQG (SEQ ID NO: 5) | SGYYEEFDS (SEQ ID NO: 6) | 3.2 |
| K3D | TYWIS (SEQ ID NO: 4) | DIYPGSGNTNYDEKFEG (SEQ ID NO: 7) | SGYYEEFDS (SEQ ID NO: 6) | 25 |

| antibody | CDRL1 | CDRL2 | CDRL3 | AFFINITY (nM) |
|---|---|---|---|---|
| IIIA4 | RASQEISGYLG (SEQ ID NO: 8) | AASTLDS (SEQ ID NO: 9) | VQYANYPYT (SEQ ID NO: 10) | 2.5 |
| FA3AM-H12A | RASQGIISYLA (SEQ ID NO: 11) | AASSLQS (SEQ ID NO: 12) | VQYANYPYT (SEQ ID NO: 10) | 3.2 |
| K3D | RASQGIISYLA (SEQ ID NO: 11) | AASSLQS (SEQ ID NO: 12) | VQYMNYPYT (SEQ ID NO: 13) | 25 | fold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Thus, Anticalins® are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49:209-216, 2003) describe a methodology for reducing antibodies into smaller peptidomimetics, they term "antibody like binding peptidomimetics" (ABiP) which may also be useful as an alternative to antibodies.

WO 00/60070 discloses a polypeptide chain having CTL4A-like β-sandwich architecture. The peptide scaffold has from 6 to 9 β-strands, wherein two or more of the polypeptide β-loops constitute binding domains for other molecules, such as antigen binding fragments. The basic design of the scaffold is of human origin, thus reducing the risk of inducing an immune response. The β-sandwich scaffold may have improved stability and pharmacokinetic properties in vivo when compared to standard antibodies as the molecule contains a second, non-immunoglobulin disulphide bridge. As antigen binding domains can be located at opposite ends of a single peptide chain, the β-sandwich also facilitates design of bispecific monomeric molecules.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody EphA3 binding agents can also include such compounds.

In some embodiments, the EphA3 binding agents employed in the invention competed with mAb IIIA4 for binding to EphA3. Such agents can be identified using known assays, such as the exemplary competition assays described herein.

Anti-EphA3 binding agents are used in a multimeric form such that they cross-link EphA3 receptors present on the surface of endothelial cells.

Treatment of Tumors

The methods of the present invention comprise administering an anti-EphA3 antibody to a patient having a tumor to inhibit tumor growth. Solid tumors that can be treated using the compositions and methods described herein include solid tumors of the breast, lung, colon, stomach, liver, kidney, ovary, and prostate. In some embodiments, the tumors do not express EphA3 on tumor cells, but express EphA3 on the tumor vasculature. In other embodiments, the tumors express EphA3 on tumor cells as well as on the tumor vasculature. Tumors that can be treated in accordance with the invention include breast carcinomas, lung carcinomas, prostate carcinomas, gastric carcinomas, esophageal carcinomas, colorectal carcinomas, liver carcinomas, ovarian carcinomas, vulval carcinomas, kidney carcinomas, cervical carcinomas, endometrial carcinoma, endometrial hyperplasia, endometriosis, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreatic carcinomas, retinoblastoma, astrocytoma, glioblastoma, Schwannoma, oligodendroglioma, medulloblastoma, neuroblastomas, sarcomas include fibrosarcomas, rhabdomyosarcoma, osteogenic sarcoma, leiomyosarcomas, urinary tract carcinomas, thyroid carcinomas, Wilm's tumor, brain tumors, renal cell carcinomas, abnormal vascular proliferation associated with phakomatoses, and edema (such as that associated with brain tumors).

In some embodiments, the methods of the present invention are used for the treatment of tumors that don't express EphA3 on tumor cells. Expression of EphA3 in tumor cells can be determined by methods well known to those of skill in the art. Often, expression is evaluated by measuring the amount of EphA3 protein expressed, e.g., using an antibody in a technique such as immunohistochemical analysis. In other embodiments, mRNA levels can be evaluated, e.g., using quantitative PCR. Little or no detectable expression, e.g., when the level of expression is about 2-fold or less than background expression, indicates that the tumor cell does not express EphA3.

The composition can be formulated for use in a variety of drug delivery systems. One or more physiologically acceptable excipients or carriers can also be included in the compositions for proper formulation. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* s249: 1527-1533 (1990).

The anti-EphA3 antibody for use in the methods of the invention is provided in a solution suitable for injection into the patient such as a sterile isotonic aqueous solution for injection. The anti-EphA3 antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

The pharmaceutical compositions of the invention are administered to a patient that has a tumor in an amount sufficient to at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose are known in the art, depending on the disease. For example, growth retardation may be indicated by absence of an increase in tumor size.

The dose of the anti-EphA3 antibody is chosen in order to provide effective therapy for the patient and is in the range of about 0.1 mg/kg body weight to about 25 mg/kg body weight or in the range about 1 mg to about 2 g per patient. The dose is often in the range of about 0.5 mg/kg or about 1 mg/kg to about 10 mg/kg, or approximately about 50 mg to about 1000 mg/patient. In some embodiments, the antibody is administered in an amount less than about 0.1 mg/kg body weight, e.g., in an amount of about 20 mg/patient or less. The dose may be repeated at an appropriate frequency which may be in the range once per day to once every three months, depending on the pharmacokinetics of the antibody (e.g. half-life of the antibody in the circulation) and the pharmacodynamic response (e.g. the duration of the therapeutic effect of the antibody). In some embodiments where the antibody or modified antibody fragment has an in vivo half-life of between about 7 and about 25 days and antibody dosing is repeated between once per week and once every 3 months. In other embodiments, the antibody is administered approximately once per month.

Amounts that are administered that are effective will depend upon the severity of the disease and the general state of the patient's health, including other factors such as age, weight, gender, administration route, etc. Single or multiple administrations of the anti-EphA3 antibody may be administered depending on the dosage and frequency as required and tolerated by the patient. In any event, the methods provide a sufficient quantity of the anti-EphA3 antibody to effectively treat the tumor.

An anti-EphA3 antibody or other anti-EphA3 binding agent that induces cross-linking of EphA3, can be used in combination with one or more additional cytotoxic agents to inhibit tumor cell growth. Cytotoxic agents are compounds that inhibit cell growth. Such compounds may or may not cause cell death. Cytoxic agents that can be administered in conjunction with anti-EphA3 binding agents include compounds such as antibodies, e.g., Her2/neu antibodies, other antibodies that target the tumor vasculature, such as VEGF antibodies; agents such as L-asparaginase, interleukins, interferons, aromatase inhibitors, antiestrogens, anti-androgens, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, protein or lipid phosphatase targeting agents, anti-angiogenic agents, anti-apoptotic pathway inhibitors, apoptotic pathway agonists, telomerase inhibitors, protease inhibitors, metalloproteinase inhibitors, and aminopeptidase inhibitors. Examples of such agents include, but are not limited to, cisplatin, cyclophosphamide, dacarbazine, ifosfamide, mechlorethamine, melphalan, carmustine, estramustine, lomustine, 5-fluorouracil, methotrexate, genistein, taxol, gemcitabine, cytarabine, fludarabine, busulfan, bleomycin, dactinomycin, daunorubicin, doxorubicin, idarubicin, epirubicin, esorubicin, detorubicin, taxanes such as paclitaxel and docetaxel, etoposide, vinca alkaloids such as vinblastine and vincristine, vinorelbine, amsacrine, tretinoin, dacarbazine (DTIC), actinomycins, maytansinol, rifamycin, streptovaricin, caminomycin, mitoxantrone, bleomycins, mitomycins, camptothecins, bortezomib, temozolomide, combretastatin, combretastatin A-2, combretastatin A-4, calicheamicins, leuprolide, and pegaspargase, fluorodeoxyuridine, ptorafur, 5'-deoxyfluorouridine, capecitabine, tamoxifen, toremefine, tolmudex, thymitaq, flutamide, fluoxymesterone, bicalutamide, finasteride, trioxifene, leuprorelin acetate, estramustine, droloxifene, megestrol acetate, aminoglutethimide, testolactone, mitomycins A, B and C, mithramycin, anthramycin, porfiromycin, carboplatin, oxaliplatin, tetraplatin, platinum-DACH, ormaplatin, thalidomide, lenalidomide, telomestatin, podophyllotoxin, epipodophyllotoxin, teniposide, aminopterin, methopterin, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, leurosine, leurosidine, vindesine, ethylenimines and methylmelamines.

In some embodiments, e.g., where an anti-EphA3 antibody is administered to a solid tumor that doesn't express EphA3, a cytotoxic cancer therapeutic composition can be linked to the antibody. Examples of such a cytotoxic agent include radiometals and toxins.

In some embodiments, the anti-EphA3 binding agent is administered with another cytotoxic composition where the administration of the anti-EphA3 binding agent facilitates the entry of the other cytotoxic compound(s) into the tumor. For example, anti-EphA3 antibodies that cross link EphA3 present on vascular endothelial cells can result in rounding of the cells and "leakiness" of the tumor vasculature. Such disruption of the vasculature allow other agents to more readily penetrate the tumor. Thus, e.g., large chemotherapeutic agents, such as polypeptides, including other antibodies, various liposome formulations, and the like are more efficacious when administered in conjunction with an anti-EphA3 binding agent that can cross-link EphA3 receptors present on the surface of endothelial cells.

In some embodiments the additional therapeutic agent is an agent that inhibits a cellular process regulated by GTP or ATP, e.g., a tubulin assembly inhibitor. The additional therapeutic agent, can be, e.g., an alpha tubulin inhibitor. Examples of alpha tubulin inhibitors include but are not limited to indanocine, indanrorine, vincistine, vinblastine, vinoreloine, combrestatinA and colichine. Other therapeutic agents commonly used for cancer treatment can also be employed with the methods of the present invention.

Patients can receive one or more of these additional therapeutic agents as concomitant therapy. Alternatively, patients may be treated sequentially with additional therapeutic agents. In some embodiments the additional therapeutic agent can be conjugated or linked to the anti-EphA3 antibody.

The invention provides methods for treatment of patients with tumor, by administering an anti-EphA3 antibody that competes for binding to EphA3 with mAb IIIA4. In some embodiments, the anti-EphA3 antibody is administered by injection or infusion through any suitable route including but not limited to intravenous, sub-cutaneous, intramuscular or intraperitoneal routes. In some embodiments, the anti-EphA3 antibody is diluted in a physiological saline solution for injection prior to administration to the patient. The antibody is administered, for example, by intravenous infusion over a period of between 15 minutes and 2 hours. In still other embodiments, the administration procedure is via sub-cutaneous, intramuscular injection or direct intra tumor injection.

The following examples are provided by way of illustration only and not by way of limitation. Those of skill in the art will readily recognize a variety of non-critical parameters that could be changed or modified to yield essentially similar results.

EXAMPLES

Example 1

Detection of EphA3 on Endothelial Cells in Tumors

Effective tumor targeting properties of the α-EphA3 monoclonal antibody (mAb) IIIA4 were recently confirmed in-vivo (Vearing, et al., *Cancer Res* 65:6745-54, 2005). Subsequent expression analysis of EphA3 in fresh-frozen sections of human lung and brain tumors and melanomas with this antibody revealed, in addition to the expected staining of tumor cells, distinct IIIA4 reactivity in tumor vessels, which were also positive for the endothelial-specific surface antigens CD31 and CD105 (FIG. 1a).

Closer inspection of other melanoma sections also indicated EphA3-positive structures reminiscent of 'vascular mimetic channels' (Hendrix, et al., Nat Rev Cancer 3:411-21, 2003). To assess endothelial EphA3 expression, various primary and established human endothelial cell lines were screened with mAb IIIA4. Consistent with the immuno-histochemical analysis of tumor sections, EphA3 was detected by flow cytometry and Western Blot on myometrial microvascular endothelial cells (m-MVECs) (Gargett, et al., Hum Reprod 15:293-301, 2000) but not on adult brain (b-) MVECS (FIG. 2) or umbilical vein endothelial cells (UVEC) (Boyd, et al. J Biol Chem 267:3262-3267, 1992), suggesting that expression may be limited to newly-emerging and tumor microvasculature.

Since a role for EphA3 in vasculogenesis has not been previously described, this represents the first indication that EphA3 is involved in adult neo-angiogenesis, vascular mimicry (Hendrix, et al., Nat Rev Cancer 3:411-21, 2003; Ogawa, et al. Oncogene 19:6043-6052, 2000; Brantley-Sieders, et al. J Cell Sci 117:2037-49, 2004) and the formation of tumor vasculature.

Example 2

EphA3 Expression Patterns on Normal and Tumor Vasculature

EphA3 Expression in Tumor Sections:
In order to assess the specificity of the illustrated endothelial IIIA4 staining pattern, the analysis was extended by including antigen competition in the experimental set up.

Figure 2A:
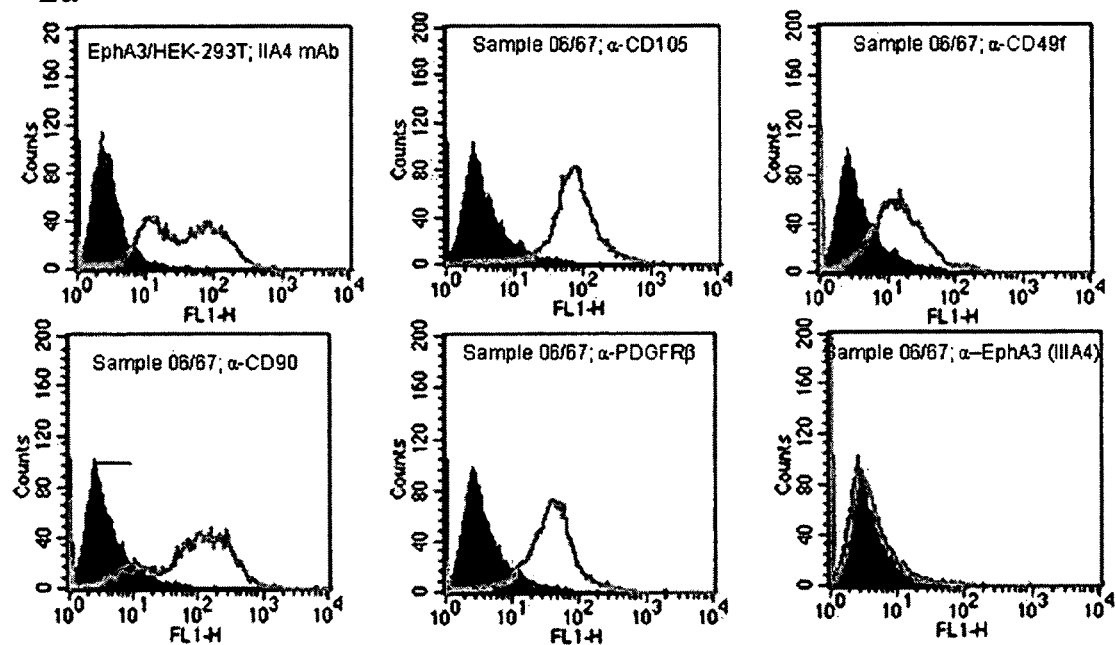
FIGS. 2a-b. Expression of EphA3 on endometrial endothelial cells is lost during extended tissue culture. (a) The expression of the various cell surface markers as well as EphA3, detected by immunocytochemical analysis in FIG. 4, was examined by flow cytometry. The EphA3 expression profile of EphA3/HEK-293T cells is shown for comparison. (b) IP/Western blot analysis of EphA3 expression in successive passages of endometrium-derived MVECS as indicated (P4-P9). EphA3 was immunoprecipitated from whole-cell lysates with IIIA4-Sepharose and Western blots probed with anti-EphA3 polyclonal antibodies.

Human melanoma sections were stained with mAb IIIA4 in the presence of 60-times molar excess of recombinant, CHO cell-produced soluble EphA3 extracellular domain. In presence of excess EphA3, strong IIIA4 staining of vascular structures/vessels was reduced to background levels, confirming the specificity of the mAb IIIA4 staining profile for EphA3 (FIG. 2a).

Confirmation of EphA3 Expression on Human Microvascular Endothelial Cells:
In order to confirm EphA3 expression on normal human microvascular endothelial cells (hMVECS, see FIG. 2) and identify a potential function of EphA3 expression in microvessel assembly, a number of strategies were developed to isolate EphA3-positive cells from endometrial tissue for their use in functional analysis.

The human endometrium consists of a simple columnar epithelium overlaying a muscular myometrium and forming numerous tubular glands supported by a thick vascular stroma. Functionally it is subdivided into two layers: (1) the 'stratum functionalis', a thick superficial layer of temporary tissue sloughed off and regenerated during each menstruation cycle, and (2) the 'stratum basalis' consisting of permanent stromal tissue and deep ends of the uterine glands, a persisting tissue that serves as cell source for during re-growth of the stratum functionalis.

In the proliferative phase, one of three stages of the cycle, spiral arterioles originating in the myometrium are elongated to span the length of the endometrium, forming the complex vascular network of the endometrium that develops during the following secretory phase.

Immunohistochemical staining of whole endo/myometrial sections from different menstrual phases with IIIA4 revealed strong EphA3 expression during the early secretory phase, especially in the endothelial and smooth muscle cells of spiral arterioles at the endometrial/mometrial junction, an area of active tissue regeneration after shedding of the stratum functionalis. This EphA3 expression pattern during the early secretory phase was confirmed in whole endometrial sections from different patients. Inclusion of excess EphA3 exodomain as competitive inhibitor in parallel samples abolished the staining pattern to background confirm the specificity of the staining for EphA3.

Example 3

Isolation of EphA3-Positive Cells from Fresh Human Endometrium

Tissue samples were obtained from patients undergoing hysterectomy as a source for EphA3-positive cells involved in the formation of early blood vessels. EphA3-expressing cells were isolated from a single-cell suspension prepared from the endometrium and ~1 mm of the underlying myometrial layer, using the 'Mylteni' magnetic affinity bead cell isolation system (MACS). Immuno-cytochemical staining of the isolated cells, cultured on fibronectin-coated glass slides with a sheep-α-EphA3 antibody suggested EphA3 expression on cells resembling by morphology pericytes, endothelial, smooth muscle cells.

Figure 2B:
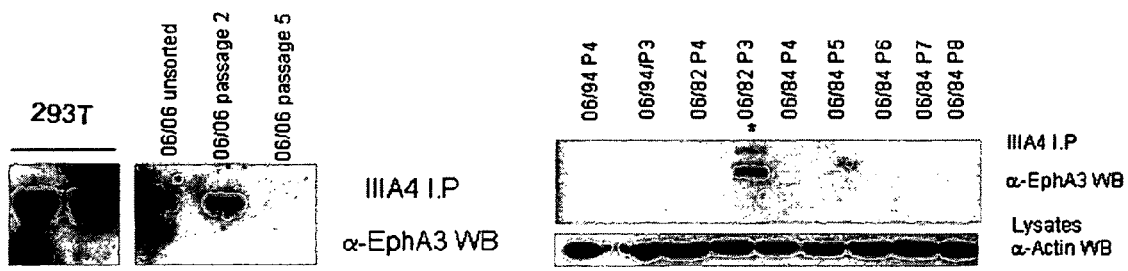

A range of molecular markers were used to verify these different cell types in the pool of EphA3$^+$ cells, using antibodies against CD105 and Ber-EP4 to identify epithelial cells, smooth-muscle actin for smooth muscle cells and CD90 and PDGF receptor-β (PDGFR-β) for stromal cells. As expected from immunohistochemical staining, the isolated pool of EphA3-positive cells is composed of several cell types involved in the assembly of blood vessels. The presence of PDGFR-β is interesting, as its expression on perivascular mesenchymal cells, pericytes and SMCs is known to be upregulated by endothelial cell-derived PDGF under various conditions including shear stress (Risau, Nature 386:671-674, 1997). Flow cytometry of the isolated cell population after expansion in tissue culture was used to confirm expression of the molecular markers that were identified by immunohistochemistry (FIG. 2a). Interestingly, at this stage the expression of EphA3 was no longer detected. Analysis of successive passages of endothelial cell derived from endometrial tissue samples by anti-EphA3 immunoprecipitation (IP)/Western blot analysis confirmed that EphA3 expression was lost after three tissue culture passages (FIG. 2b).

Figure 3A:
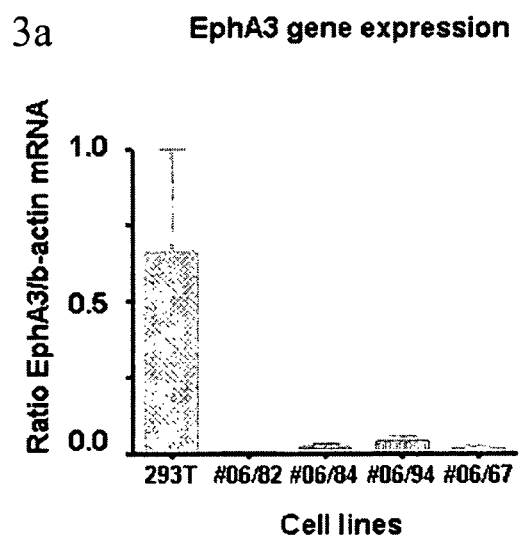
FIG. 3. Estimation of EphA3 mRNA expression levels by quantitative real-time PCR. Total mRNA was extracted from mMVECS isolated from various endometrial tissue samples. The levels of β-actin were determined in parallel as internal reference, while mRNA from HEK293T cells served as a positive control for EphA3 expression, expressed as ratio between β-actin and EphA3 mRNA levels. Mean and SD from three independent samples are illustrated.

EphA3 expression was further confirmed in the different tissue samples by quantitative real-time PCR to detect the mRNA expression levels, using β-actin mRNA as an internal control house-keeping gene, and HEK293T cells as a positive control for EphA3 expression. The data illustrated in FIG. 3a reveal detectable EphA3 expression in the different sample types. The apparently transient expression pattern in tissue sections and loss of EphA3 expression during tissue culture suggests that expression is regulated by the local environment of the cell population.

Figure 3B:
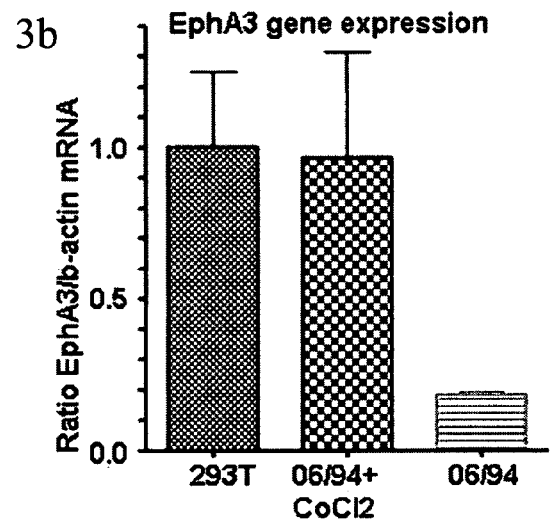

To examine one of the potential triggers, hypoxia, EphA3-positive cells were treated with $CoCl_2$, a well-established method for chemically-induced hypoxia in-vitro. Indeed, this treatment resulted in a pronounced increase in EphA3 mRNA (FIG. 3b).

Example 4

EphA3 Function in Normal and Tumor Vasculature

Functional Analysis of EphA3-Positive Endometrial Cells.

To study the potential cell positioning function of EphA3 during vessel formation, EphA3-positive and negative as well as CD34 positive and negative cells were purified through successive rounds on Mylteni magnetic beads. Labeling of the purified cells with vital dyes allowed monitoring cell movements and position during the formation of blood vessel-like structures in growth-factor-reduced matrigel in situ. By adding fluorescent labeled, double-positive or negative cell populations to mixed, EphA3-positive or negative cell populations from the same tissue samples, allowed an assessment of EphA3 function during the formation of vascular structures in-vitro. Analysis of the matrigel plugs after 24 h culture by multiphoton fluorescence microscopy revealed distinctive three-dimensional structures outlined by the fluorescent cells, in particular in samples containing EphA3-positive cells. A more detailed immunohistochemical analysis of OTC-frozen sections the Marigel blocks suggests that the presence of EphA3-positive cells is required for the formation of extensively-branched vascular structures.

Overall, this analysis supports the notion of a cell positioning role of EphA3 during blood vessel assembly, possibly facilitating the formation of contacts between the different cell types involved vascularization, including endothelial, smooth muscle and perivascular mesenchymal cells.

Example 5

Figure 4A:
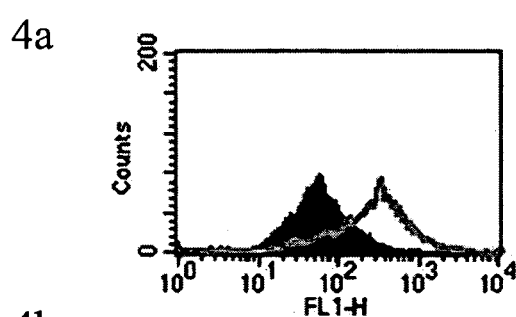
FIGS. 4a-c. Expression of EphA3 in human 22RV1 prostate carcinoma cells. (a) EphA3 expression was examined by flow cytometry, using mAb IIIA4 and fluorescine-conjugated anti-mouse antibody for detection. (b) The levels of EphA3 expression was estimated and compared to the expression in EphA3/HEK293T cells by IP/Western Blot analysis of whole cell lysates. In parallel samples the EphA3 tyrosine phosphorylation following stimulation of cells with pre-clustered ephrin-A5 Fc or ch-IIIA4 was assessed using an anti-PY EphA3 polyclonal antibody for Western blot analysis. (c) 22RV1 cells were cultured on fibronectin-coated glass slides and incubated with Alexa$^{546}$IIIA4 in the presence or absence of ephrin-A5 Fc, as indicated. The actin cytoskeleton of fixed and permeabilised cells was stained with Alexa$^{488}$Phalloidin.
Figure 4B:
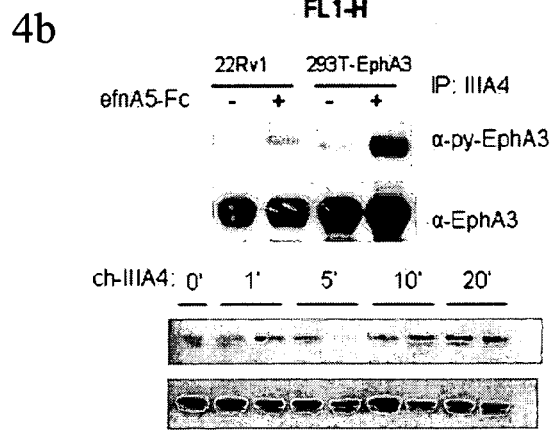
Figure 4C:
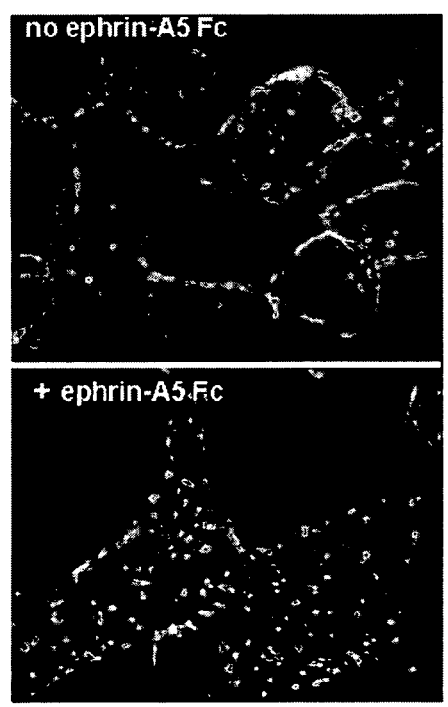

Intravital Imaging of IIIA4 Targeting of EphA3-Positive Xenograft Tumors Reveals EphA3 Expression and IIIA4 Targeting of the Tumor Vasculature In view of the expression of EphA3 in the tumor vasculature of solid tumors and a role of EphA3 in blood vessel assembly indicated from the experiments described above, the therapeutic potential of mAb IIIA4 α-EphA3 as anti-neoangiogenic reagent was investigated. For these studies, the 22RV1 prostate carcinoma cell line was employed, which is known to produce vascularized, metastasizing xenografts in nude mice. Analysis by Q-PCR (not shown), Western blot (FIG. 4a), flow cytometry (FIG. 4b) and immunocytochemistry (FIG. 4c) revealed significant levels of endogenous EphA3.

Furthermore, stimulation with a combination of Alexa$^{488}$-labelled mAb IIIA4 and ephrin-A5 Fc (Vearing, et al., Cancer Res 65:6745-54, 2005) resulted in moderate EphA3 activation, but rapid and pronounced internalization of the receptor/agonist complexes (FIG. 4 b/c). In addition, it was confirmed that also pre-clustered mouse/human chimeric IIIA4 triggered notable EphA3 activation (phosphorylation) in these cells. Co-staining of sections prepared from EphA3/HEK293T xenografts (Vearing, et al., Cancer Res 65:6745-54, 2005) or 22RV1 xenografts with pan-specific Rhodamine-RCA lectin (binding to endothelial cells) (Hunter, et al., Mol Cancer 5:5, 2006) and with Alexa$^{488}$ labelled mouse/human chimeric IIIA4 (ch-IIIA4) revealed expression of EphA3 on some of the endothelial cells. Intravital image analysis of 22RV1 tumor xenograft-bearing mice was used to visualize the binding of Alexa$^{488}$-IIIA4 to EphA3-positive cells and blood vessels.

Antibody-conjugated fluorescence outlining a substantial number of tumor blood vessels demonstrated that the IIIA4 antibody targets tumor blood vessels. Subsequent perfusion of the vasculature with pan-specific Rhodamine-RCA lectin or Isolectin IB4-Alexa$^{594}$ binding to endothelial cells (Hunter, et al., Mol Cancer 5:5, 2006) confirmed that only a distinct subset of blood vessels had been labelled with the Alexa$^{488}$-IIIA4. Immunofluorescence analysis of frozen 22RV1 sections from these mouse xenografts (following intravital imaging) confirmed co-localized IIIA4 and RCA-lectin staining in a significant proportion of the analyzed cells. Monoclonal antibody IIIA4 is an antibody with a relatively inactive (murine IgG1) isotype.

In contrast, a chimeric IIIA4 antibody that has an active (human IgG1) isotype binds to Fc-receptors on mouse blood cells as well as on human blood cells. When the chimeric IIIA4 was conjugated to Alexa$^{488}$-labeled Quantum Dots (Invitrogen) and injected into 22RV1 tumor xenograft-bearing mice, significant disruption of the tumor vasculature was observed. Dispersal of the antibody-Quantum Dot conjugate into the tumor mass was detected both by intravital imaging and by subsequent immunofluorescence analysis of frozen tumor sections whereas Quantum Dot conjugate with mouse IIIA4 was retained within the blood vessels.

Example 6

Fc-Receptor-Mediated Cross-Linking of EphA3 In Vitro

Cross-linking anti-EphA3 antibody bound to cells can lead to cell-rounding, a mechanism by which tumor neo-vasculature can be disrupted.

To establish conditions for EphA3-mediated cell-rounding in vitro, human LiBR melanoma cells (ATCC) were treated with 0.1 μg/ml chimeric IIIA4 and incubated at 37° C. with $CO_2$ for 10 minutes. The cells were washed to remove unbound antibody and 0.05 μg/ml of polyclonal rabbit anti-human IgG antibody was added to induce cross-linking of cell-bound cIIIA4. After incubating for 30 minutes at 37° C. with $CO_2$, cells exhibited a rounded morphology compared to the spindle-shaped cells treated with cIIIA4 without cross-linking antibody.

Cross-linking of cell-bound anti-EphA3 antibody can also be achieved by incubating EphA3-positive target cells with 0.05-0.1 μg/ml anti-EphA3 antibody and human peripheral blood mononuclear cells (PBMC) expressing Fc-receptors. For this purpose, heparinized blood or buffy coats (Stanford Blood Center, Palo Alto, Calif.) were diluted in calcium- and magnesium-free PBS before layering over Ficoll-Paque (GE Healthcare) density cell separation material. Thirty five milliliters of diluted blood samples were carefully layered over 15 ml of Ficoll-paque in 50 ml centrifuge tubes. Layered blood samples were centrifuged in Allegra 6R Centrifuge (Beckman Coulter) for 30 minutes at 2150 RPM without the break on. PBMC collecting at the interface were transferred to another 50 ml centrifuge tube using 10 ml pipets and washed four times in PBS at a lower speed (1000 RPM). Cells were counted in trypan blue stain and used in the assays. LiBr tumor target cells ($2 \times 10^4$/well) were cultured in 24 well tissue culture plates (Costar, Corning Inc.) at 37° C. in a 5% $CO_2$ incubator for 24 hours in culture medium, washed once with medium and incubated with anti-EphA3 antibody at 0.05 μg/ml for 30 minutes on ice. Cells were washed twice with medium to remove unbound antibody and dead cells. PBMC were used as effector cells (for antibody cross-linking) in the assay. Effector cells were added to the target cells at a ratio of 1:1 (40,000 effector cells) or 10:1 (400,000 effector cells) and incubated at 37° C. in a 5% $CO_2$ incubator for 10 to 30 minutes. Target-cell rounding was assessed under microscope. Significant PBMC-dependent cell-rounding was observed in anti-EphA3-treated cells, with an effector:target ratio of 10:1, detectable after 10 minutes incubation and pronounced cell-rounding was observed after 30 minutes.

Example-7

Inhibition of Growth of a Human Tumor Xenograft Expressing EphA3 on the Tumor Vasculature but not on Tumor Cells The human prostate cancer cell line DU-145 (ATCC catalog number HTB-81) was chosen as an example of a tumor type that does not express EphA3 on the tumor cell surface. Sensitive immunohistochemical analysis confirmed that DU-145 tumors grown as xenograft tumors in nude mice do not express detectable EphA3 antigen on the tumor cells. In contrast, EphA3 is detected on the surface of endothelial cells within the tumor mass. To determine the effect of binding of anti-EphA3 antibody to tumor vasculature on the growth of tumors in vivo, chimeric IIIA4 antibody was used to treat DU-145 tumor xenografts.

Chimeric IIIA4 antibody was generated by fusion of coding sequences for the heavy chain V-region of IIIA4 to human gamma-1 constant region and the light chain V-region coding sequences to human kappa constant region sequences. Chimeric heavy and light chains were expressed under the control of hCMV-MIE promoter-enhancers in CHO—S cells (Invitrogen) and antibody was purified by Protein A affinity chromatography according to standard methods. Binding of cIIIA4 antibody to human and murine EphA3 was confirmed by antigen-binding ELISA.

DU-145 cells were passaged in male athymic nude carrier mice (*Mus musculus* strain NCR nu/nu; Simonsen Laboratories Inc, Gilroy, Calif.). Tumor fragments 1-5 mm$^3$ in size were then delivered sub-cutaneously to the upper dorsum of male nude mice and allowed to form tumors. Tumor volume was determined using vernier calipers and established tumors, 40-60 mm$^3$ in size, were arbitrarily assigned to study groups (10 mice per group).

Mice with established tumors were dosed with chimeric IIIA4 antibody (10 mg/kg) by intraperitoneal (i.p.) administration or vehicle control twice weekly for 6 weeks. Tumor dimensions were measured using calipers twice weekly during the course of the study and tumor weights were recorded at necropsy.

Figure 5:
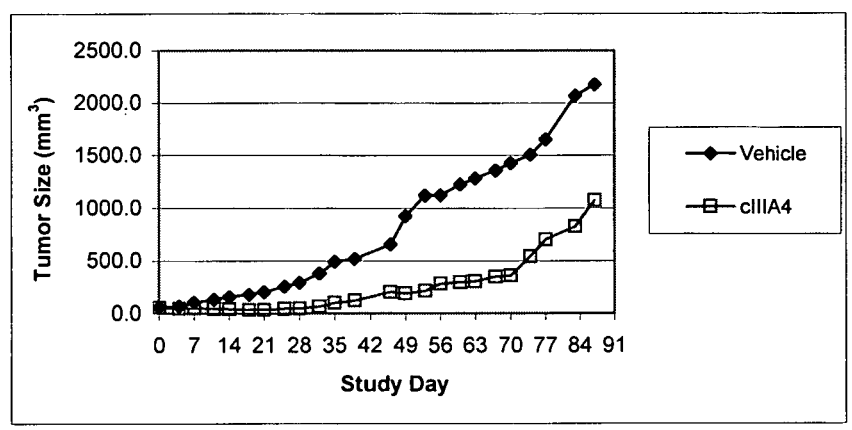
FIGS. 5a-b. Anti-EphA3 antibody inhibits the growth of EphA3 antigen-negative tumor xenografts in vivo. Nude mice bearing human DU-145 prostate cancer cells were treated twice weekly for 6 weeks with chimeric IIIA4 antibody (10 mg/kg; i.p.) or vehicle control. a) mean tumor volumes (determined using vernier calipers) up to 50 days after the end of treatment. b) tumor weights (mean±standard deviation) at necropsy 50 days after the end of treatment.
Figure 5:
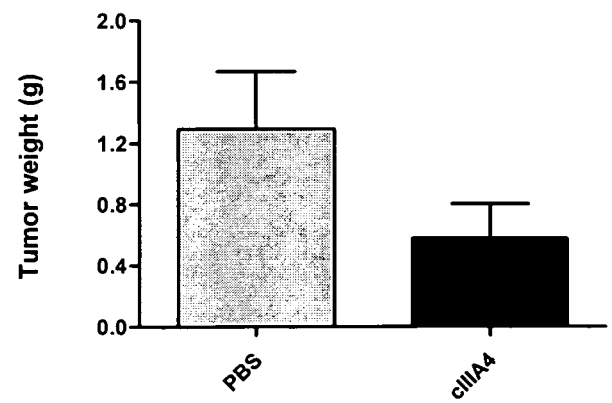

Tumor growth rates are shown in FIG. 5a. Significant inhibition of tumor growth was evident in the anti-EphA3-treated animals. Differences in tumor size between the 2 groups were statistically significant (Student's t-test; P<0.05) on Days 11-74 of the in-life phase.

Analysis of individual animals indicated that complete tumor regression occurred in 3 antibody-treated animals such that the tumors were non-palpable in these 3 animals by 20 days of treatment. Two of these tumors subsequently re-grew but one animal showed permanent tumor regression with tumor remaining undetectable 50 days after the end of treatment. Histological analysis at necropsy demonstrated no detectable residual tumor in this animal. In contrast, all tumors in the vehicle control group showed continued growth throughout the study.

Mean tumor weights for tumors dissected 50 days after cessation of antibody treatment are shown in FIG. 5b.

These results demonstrate that chimeric IIIA4 antibody to EphA3 is effective in the treatment of tumors in which EphA3 is expressed on tumor vasculature.

Example-8

Treatment of an EphA3-Positive Human Tumor Xenograft with cIIIA4

The human prostate cancer cell line LNCaP (ATCC catalog number CRL-1740) was chosen as an example of a tumor type that expresses EphA3 on the tumor cell surface.

LNCaP cells were passaged in male athymic nude carrier mice (*Mus musculus* strain NCR nu/nu; Simonsen Laboratories Inc, Gilroy, Calif.). Tumor fragments 1-5 mm$^3$ in size were delivered sub-cutaneously to the upper dorsum of male nude mice and allowed to form tumors. Mice with established tumors 40-60 mm in size were arbitrarily assigned to study groups (10 mice per group) and dosed with chimeric IIIA4 antibody (10 mg/kg) by intraperitoneal (i.p.) administration or vehicle control twice weekly for 6 weeks. Tumor dimensions were measured using calipers twice weekly during the course of the study and tumor weights were recorded at necropsy.

Figure 6:
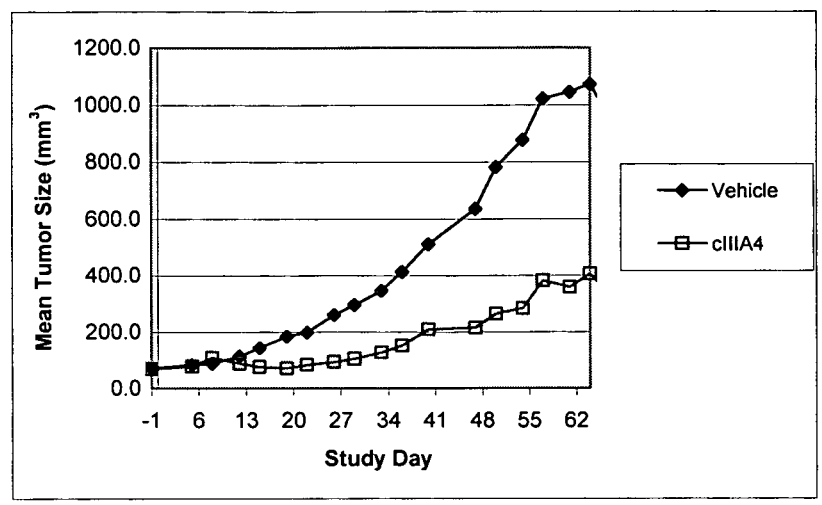
FIGS. 6a-b. Anti-EphA3 antibody inhibits the growth of EphA3 antigen-positive tumor xenografts in vivo. Nude mice bearing human LNCaP prostate cancer cells were treated twice weekly for 6 weeks with chimeric IIIA4 antibody (10 mg/kg; i.p.) or vehicle control. a) mean tumor volumes (determined using vernier calipers) up to 22 days after the end of treatment. b) tumor weights (mean±standard deviation) at necropsy 25 days after the end of treatment.
Figure 6:
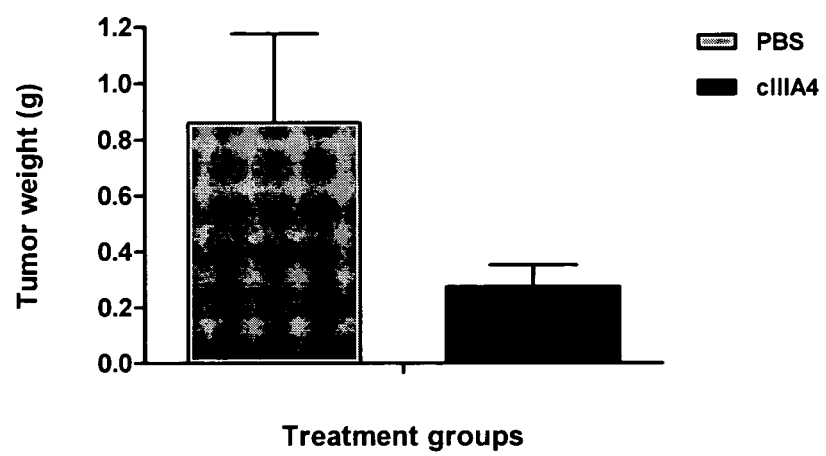

Tumor growth rates are shown in FIG. 6a. Significant inhibition of tumor growth was evident in the anti-EphA3-treated animals. Differences in tumor size between the 2 groups were statistically significant (repeated measures ANOVA with a post-hoc Bonferroni's test).

Analysis of individual animals indicated that complete tumor regression occurred in 2 antibody-treated animals such that the tumors were non-palpable in these animals by 25 days of treatment. Long-term tumor eradication was observed in these two animals with tumor remaining undetectable 25 days after the end of treatment. Histopathology demonstrated that no detectable tumor remained in these two animals at the end of the study. In contrast, all animals in the vehicle control group showed continued tumor growth throughout the study.

Mean tumor weights for tumors dissected 25 days after cessation of antibody treatment are shown in FIG. 6b.

These results demonstrate that chimeric IIIA4 antibody to EphA3 is effective in the treatment of tumors in which EphA3 is expressed on the tumor cells as well as on tumor vasculature.

Example 9

Evaluation of EphA3 in Human Tumor Samples

Immunohistochemistry was carried out on a range of human tumor samples using mAb IIIA4. Anti-EphA3 antibody was incubated with frozen sections of tumor samples at 8 µg/ml for 90 minutes at room temperature and binding was revealed by a Vectastain immunohistochemistry kit. Substantial EphA3 expression was detected on the tumor vasculature in a number of tumor types as shown in the Table 2.

TABLE 2

Expression of EphA3 on tumor vasculature.

| Tumor | Vessel staining | Positive samples |
| --- | --- | --- |
| Renal cell carcinoma | ++ | 5/5 |
| Lung adenocarcinoma | ++ | 4/5 |
| melanoma | +++ | 14/15 |
| Glioblastoma multiforme | +++ | 4/6 |
| Breast: infiltrating ductal carcinoma | +/++ | 5/6 |

All publications, patent applications, accession numbers, and other references cited in this specification are herein incorporated by reference as if each individual publication or patent application were specifically and individually indicated to be incorporated by reference.

---

What is claimed is:

1. A method of inhibiting growth of a solid tumor in a subject that has a solid tumor that expresses EphA3 on the tumor vasculature, but has fewer than 25% of tumor cells that have detectable expression of EphA3 on the tumor cell surface, the method comprising administering an anti-EphA3 antibody that clusters and activates EphA3 to the subject, with the proviso that the anti-EphA3 antibody is not conjugated to a therapeutic agent.

2. The method of claim 1, wherein less than 10% of the tumor cells have detectable expression of EphA3 on the cell surface.

3. The method of claim 1, wherein the anti-EphA3 antibody competes for EphA3 binding with an antibody that has a $V_H$ region CDR1 SYWIN (SEQ ID NO:1), a $V_H$ region CDR2 DIYPGSGNTNYDEKFKR (SEQ ID NO:2), a $V_H$ region CDR3 SGYYEDFDS (SEQ ID NO:3), a $V_L$ region CDR1 RASQEISGYLG (SEQ ID NO:8), a $V_L$ region CDR2 AASTLDS (SEQ ID NO:9), and a $V_L$ region CDR3 VQYANYPYT (SEQ ID NO:10).

4. The method of claim 1, wherein the anti-EphA3 antibody is a recombinant or chimeric antibody.

5. The method of claim 1, wherein the anti-EphA3 antibody is a human antibody.

6. The method of claim 1, wherein the anti-EphA3 antibody is a humanized antibody or an engineered antibody that comprises sequences from human $V_H$- and $V_L$-segments.

7. The method of claim 1, wherein the anti-EphA3 antibody is a monoclonal antibody.

8. The method of claim 1, wherein the anti-EphA3 antibody is a multivalent antibody that comprises an antibody fragment that is a Fab, a Fab', or an Fv.

9. The method of claim 1, wherein the anti-EphA3 antibody comprises a human Fc region.

10. The method of claim 9, wherein the anti-EphA3 antibody comprises a human gamma 1 or gamma 3 active isotype.

11. The method of claim 10, wherein the Fc region glycosylation lacks fucose.

12. The method of claim 1, wherein the anti-EphA3 antibody comprises a $V_H$ region CDR1 SYWIN (SEQ ID NO:1), a $V_H$ region CDR2 DIYPGSGNTNYDEKFKR (SEQ ID NO:2), a $V_H$ region CDR3 SGYYEDFDS (SEQ ID NO:3), a $V_L$ region CDR1 RASQEISGYLG (SEQ ID NO:8), a $V_L$ region CDR2 AASTLDS (SEQ ID NO:9), and a $V_L$ region CDR3 VQYANYPYT (SEQ ID NO:10).

13. The method of claim 1, wherein the anti-EphA3 antibody comprises:
a $V_H$ region CDR1 TYWIS (SEQ ID NO:4), a $V_H$ region CDR2 DIYPGSGNTNYDEKFQG (SEQ ID NO:5), a $V_H$ region CDR3 SGYYEEFDS (SEQ ID NO:6), a $V_L$ region CDR1 RASQGIISYLA (SEQ ID NO:11), a $V_L$ region CDR2 AASSLQS (SEQ ID NO:12), and a $V_L$ region CDR3 VQYANYPYT (SEQ ID NO:10); or
a $V_H$ region CDR1 TYWIS (SEQ ID NO:4), a $V_H$ region CDR2 DIYPGSGNTNYDEKFEG (SEQ ID NO:7), a $V_H$ region CDR3 SGYYEEFDS (SEQ ID NO:6), a $V_L$ region CDR1 RASQGIISYLA (SEQ ID NO:11), a $V_L$ region CDR2 AASSLQS (SEQ ID NO:12), and a $V_L$ region CDR3 VQYMNYPYT (SEQ ID NO:13).

14. The method of claim 1, further comprising administering a cancer therapeutic agent.

15. The method of claim 14, wherein the cancer therapeutic agent inhibits tubulin assembly.

16. A method of inhibiting growth of a solid tumor in subject that has a solid tumor that expresses EphA3 on tumor vasculature, but does not express detectable EphA3 on the surface of tumor cells, the method comprising administering an anti-EphA3 antibody to the patient.

17. The method of claim 16, wherein the antibody clusters and activates EphA3.

18. A method of claim 17, wherein the anti-EphA3 antibody competes for EphA3 binding with an antibody that has a V region CDR1 SYWIN (SEQ ID NO:1), a $V_H$ region CDR2 DIYPGSGNTNYDEKFKR (SEQ ID NO:2), a $V_H$ region CDR3 SGYYEDFDS (SEQ ID NO:3), a $V_L$ region CDR1 RASQEISGYLG (SEQ ID NO:8), a $V_L$ region CDR2 AASTLDS (SEQ ID NO:9), and a $V_L$ region CDR3 VQYANYPYT (SEQ ID NO:10).

19. The method of claim 16, wherein the anti-EphA3 antibody is a monoclonal antibody.

20. The method of claim 16, wherein the anti-EphA3 is a recombinant or chimeric antibody.

21. The method of claim 16, wherein the anti-EphA3 antibody is a human antibody.

22. The method of claim 16, wherein the anti-EphA3 antibody is a humanized antibody or an engineered antibody that comprises sequences from human $V_H$- and $V_L$-segments.

23. The method of claim 16, wherein the anti-EphA3 antibody comprises a human Fc region.

24. The method of claim 23, wherein the anti-EphA3 antibody comprises a human gamma-1 or gamma-3 active isotype.

25. The method of claim 24, wherein the anti-EphA3 antibody Fc region glycosylation lacks fucose.

26. The method of claim 16 wherein the anti-EphA3 antibody is a multivalent antibody that comprises an antibody fragment that is a Fab, a Fab', or an Fv.

27. The method of claim 16, wherein the anti-EphA3 antibody has a $V_H$ region CDR1 SYWIN (SEQ ID NO:1), a $V_H$ region CDR2 DIYPGSGNTNYDEKFKR (SEQ ID NO:2), a $V_H$ region CDR3 SGYYEDFDS (SEQ ID NO:3), a $V_L$ region CDR1 RASQEISGYLG (SEQ ID NO:8), a $V_L$ region CDR2 AASTLDS (SEQ ID NO:9), and a $V_L$ region CDR3 VQYANYPYT (SEQ ID NO:10).

28. The method of claim 16, wherein the anti-EphA3 antibody comprises:
a $V_H$ region CDR1 TYWIS (SEQ ID NO:4), a $V_H$ region CDR2 DIYPGSGNTNYDEKFQG (SEQ ID NO:5), a $V_H$ region CDR3 SGYYEEFDS (SEQ ID NO:6), a $V_L$ region CDR1 RASQGIISYLA (SEQ ID NO:11), a $V_L$ region CDR2 AASSLQS (SEQ ID NO:12), and a $V_L$ region CDR3 VQYANYPYT (SEQ ID NO:10); or
a $V_H$ region CDR1 TYWIS (SEQ ID NO:4), a $V_H$ region CDR2 DIYPGSGNTNYDEKFEG (SEQ ID NO:7), a $V_H$ region CDR3 SGYYEEFDS (SEQ ID NO:6), a $V_L$ region CDR1 RASQGIISYLA (SEQ ID NO:11), a $V_L$ region CDR2 AASSLQS (SEQ ID NO:12), and a $V_L$ region CDR3 VQYMNYPYT (SEQ ID NO:13).

29. The method of claim 16, further comprising administering a cancer therapeutic agent.

30. The method of claim 29, wherein the cancer therapeutic agent inhibits tubulin assembly and further, wherein anti-EphA3 antibody clusters and activates EphA3.

* * * * *